United States Patent [19]

Bank

[11] Patent Number: 4,780,555

[45] Date of Patent: Oct. 25, 1988

[54] METHOD FOR PREPARING AND STABILIZING ACRYL-FUNCTIONAL HALOSILANES

[75] Inventor: Howard M. Bank, Freeland, Mich.

[73] Assignee: Dow Corning Corporation, Midland, Mich.

[21] Appl. No.: 140,442

[22] Filed: Jan. 4, 1988

[51] Int. Cl.$^4$ .............................................. C07F 7/08
[52] U.S. Cl. ...................................... 556/440; 556/401
[58] Field of Search ............................... 556/440, 401

[56] References Cited

U.S. PATENT DOCUMENTS

| | | | |
|---|---|---|---|
| 3,188,300 | 6/1965 | Chalk | 556/401 X |
| 3,803,140 | 4/1974 | Cook et al. | 556/401 X |
| 3,816,267 | 6/1974 | Chuang | 556/401 X |
| 3,925,434 | 12/1975 | Chuang | 260/448.2 |
| 4,021,310 | 5/1977 | Shimizu et al. | 203/3 |
| 4,503,208 | 3/1985 | Zin et al. | 556/440 X |
| 4,558,111 | 12/1985 | Tolentino | 77/04 |
| 4,709,067 | 11/1987 | Chu et al. | 556/440 |

FOREIGN PATENT DOCUMENTS 0736504  6/1966  Canada ............................... 556/401

Primary Examiner—Paul F. Shaver
Attorney, Agent, or Firm—Alexander Weitz

[57] ABSTRACT

There is disclosed a method for preparing acryl-functional halosilanes by reacting a halosilane with an acryloxy or methacryloxy-functional organic compound in the presence of a platinum hydrosilation catalyst and a stabilizing amount of phenothiazine, wherein the reaction mixture is contacted with an oxygen-containing inert gas. The present invention further discloses a method for stabilizing the above reaction mixture by contacting it with the oxygen-containing gas.

20 Claims, No Drawings

METHOD FOR PREPARING AND STABILIZING ACRYL-FUNCTIONAL HALOSILANES

The present invention relates to a method for preparing acryl-functional halosilanes. More particularly, the present invention relates to a method for reacting a halosilane with an acryl-functional organic compound in the presence of a platinum hydrosilation catalyst and a stabilizing amount of phenothiazine, wherein the reaction mixture is contacted with an oxygen-containing inert gas. The present invention further relates to a method for stabilizing the above reaction mixture by contacting it with the oxygen-containing gas.

BACKGROUND OF THE INVENTION

Organic compounds containing acrylic groups are well known to require protection from heat during their processing, storage and use as reaction intermediates. Such protection is generally afforded by the addition of a small quantity of a stabilizing compound to the organic compound. Thus, for example, in U.S. Pat. No. 4,021,310 to Shimizu et al., a method for inhibiting the polymerization of acrylic acid or acrylic esters during distillation is disclosed. Here, the distillation is carried out in the presence of (A) at least one compound selected from hydroquinone, hydroquinone monomethyl ether, cresols, phenols, t-butyl catechol, diphenylamine, phenothiazines and methylene blue; (B) at least one compound selected from copper dimethyldithiocarbamate, copper diethyldithiocarbamate, copper dibutyldithiocarbamate and copper salicylate; and (C) molecular oxygen. This patent does not suggest that this method is applicable to the stabilization of any silicon compound, much less an acryl-functional halosilane.

It is also known that acryl-functional halosilanes are particularly susceptible to thermal polymerization during their preparation and subsequent purification by distillation. Furthermore, safety considerations often dictate that oxygen levels be kept low during the preparation and distillation of acryl-functional halosilanes in view of the potential of fire or explosion. With this observation in mind, some compounds which do not require the presence of oxygen in order to act as stabilizers for the acryl-functional halosilanes, such as phenothiazine, have been employed in the art. This is exemplified by U.S. Pat. No. 4,558,111. In this patent, Tolentino discloses a method for making acrylate-functional halosilanes or halosiloxane by reacting an organic acrylate and a halosilane or halosiloxane having at least one silicon-bonded hydrogen atom. The reaction takes place in the presence of a hydrosilation catalyst and an amount of inhibitor effective for preventing the thermal free radical polymerization of the organic acrylate. This disclosure mentions at least seven inhibitors and illustrates the preparation of different chlorosilanes using phenothiazine as the inhibitor while purging the reaction flask with nitrogen.

SUMMARY OF THE INVENTION

It has now been found that when certain acryl-functional halosilanes are prepared in the presence of a platinum hydrosilation catalyst and a stabilizing amount of phenothiazine, the use of a nitrogen purge, as taught by the above cited patent to Tolentino, affords little protection from thermal polymerization, and subsequent gelation. Unexpectedly, it has been discovered that, when a small amount of oxygen is included in the purge gas, the desired stability is achieved. The present invention, therefore, relates to a method for making an acryl-functional halosilane having the general formula

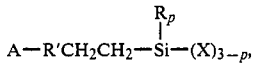

comprising reacting an unsaturated organic compound having the formula

with a halosilane having the formula

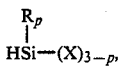

in which A is a group selected from acryloxy or methacryloxy radicals, R' is selected from a divalent hydrocarbon radical having 1 to 11 carbon atoms, an aryl group or an aryl-containing alkylene group, R is selected from alkyl radicals having 1-6 carbon atoms or the phenyl radical, X is selected from chlorine or bromine radicals and p is 0, 1 or 2, in the presence of a platinum hydrosilation catalyst and a stabilizing amount of phenothiazine, wherein the reaction mixture is contacted with a gas composition comprising at least 0.1 percent by volume of oxygen.

The present invention further relates to a method for stabilizing a mixture of the above mentioned acryl-functional halosilane, halosilane, platinum hydrosilation catalyst and phenothiazine, wherein the mixture is contacted by the oxygen-containing gas composition.

DETAILED DESCRIPTION OF THE INVENTION

In one respect, this invention relates to a method for preparing an acryl-functional halosilane having a functional moiety selected from the acryloxy or methacryloxy radicals in its molecule. In the method of the present invention, a stabilizing amount of phenothiazine is added during the preparation of the acryl-functional halosilane and an oxygen-containing inert gas is used to contact the reaction mixture to reduce its thermal polymerization tendencies. This invention also relates to the stabilization of an acryl-functional halosilane, again employing the combination of phenothiazine and the oxygen-containing inert gas.

The acryl-functional halosilanes which are advantageously prepared and/or stabilized by the methods of the present invention may be represented by the general formula

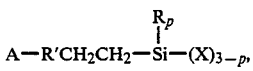

wherein A is a group selected from acryloxy or methacryloxy radicals, preferably methacryloxy. In the above formula, R' is a saturated divalent hydrocarbon radical having 1 to 11 carbon atoms. Alkylene groups such as methylene, ethylene, propylene, isopropylene, butylene, isobutylene, 2—ethylhexylene, decylene and octylene are specific examples of R'. Alternatively, R' may be an aryl group such as phenylene and naphthalene, or an aryl-containing alkylene group such as —(C₆H-

4)—$CH_2$—. Preferably, R' is the methylene group. The group R is selected from alkyl radicals having 1–6 carbon atoms or the phenyl radical. Preferably, R is the methyl radical, hereinafter designated as Me. The group X is selected from chlorine or bromine radicals, preferably chlorine. The value of p is 0, 1 or 2, preferably 0. It is further preferred that A is the methacryloxy group.

Specific examples of acryl-functional halosilanes containing acryloxy or methacryloxy groups include 3-methacryloxypropyltrichlorosilane, 3-methacryloxypropyldimethylchlorosilane, 3-methacryloxypropylmethyldichlorosilane, 3-acryloxypropyltrichlorosilane and the structure $(Cl)_3SiCH_2CH_2$—$(C_6H_4)$—$CH_2OC(O)C(Me)$=$CH_2$.

For the purposes of the present invention, the acryl-functional halosilanes are prepared by reacting an unsaturated organic compound having the formula A—R'CH=$CH_2$ with a halosilane, having the formula

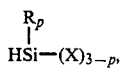

in the presence of a platinum hydrosilation catalyst and a stabilizing amount of phenothiazine, as described by Tolentino, cited supra and hereby incorporated by reference. In these formulas, the symbols have their previously defined meanings. For the purposes of the present invention, the platinum hydrosilation catalyst may be selected from chloroplatinic acid or complexes thereof, all well known in the art. A preferred catalyst consists essentially of a chloroplatinic acid complex of divinyltetramethyldisiloxane which may be prepared according to the methods of U.S. Pat. No. 3,419,593 to Willing, hereby incorporated by reference. Unlike the examples suggested by Tolentino, however, it has been found that gel-free production of acryl-functional halosilane only results when the above reaction mixture is contacted with an inert gas which contains molecular oxygen. When no oxygen is supplied to the reaction mixture, increased viscosity, gel formation and, even total gelation of the mixture can result. While not wishing to be bound by a particular theory or mechanism, it is believed that, although phenothiazine is a good stabilizer for the pure acryl-functional halosilane in the absence of oxygen, its effectiveness is somehow lost in the presence of the other components utilized in the above reaction. This is particularly the case when the halosilane is present in excess of stoichiometric proportions. Such an excess would be present, albeit on a local level and in small measure, in the methods advocated by the patent to Tolentino, cited supra, wherein the halosilane is added dropwise to a combination of the unsaturated organic compound, phenothiazine and hydrosilation catalyst.

Thus, one aspect of the present invention is a method for carrying out the above reaction such that the reaction mixture is contacted with a gas composition comprising at least 0.1% by volume of oxygen, the remainder of the gas composition being selected from any of the commonly employed inert gases known in the art. The term "inert" as used herein signifies that the gas will not react with any of the components in the reaction mixture. Specific examples of suitable inert gases include nitrogen, helium, argon and carbon dioxide. Preferably, the inert gas is nitrogen. It will, of course, be recognized by those skilled in the art that the inert gas as well as the oxygen mixed therewith must be substantially free of moisture, since water would react with the halosilane or acryl-functional halosilane. From a safety perspective, it is generally preferred to carry out the above reaction at as low an oxygen content as possible since the halosilanes can be quite volatile and pose considerable fire and explosion hazards. It is thus contemplated that the gas composition could be ordinary (dry) air if safety aspects so permit. However, a preferred range of oxygen content in the gas composition used to contact the reaction mixture is from about 2–4% oxygen by volume, most preferably 2%. For the purposes of the present invention, the manner in which the oxygen-containing gas composition is contacted with the reaction mixture is not critical and may comprise purging the reaction vessel with the gas composition, blanketing said reaction mixture with the gas composition, preferably, sparging the gas composition through the reaction mixture. As those skilled in the art will appreciate, the above reaction may be practiced as a batch or continuous operation.

In another aspect, the present invention provides a method for stabilizing the acryl-functional halosilane in the presence of the unsaturated organic compound, the halosilane, the platinum hydrosilation catalyst and a stabilizing amount of phenothiazine. Such a mixture, herein referred to as crude acryl-functional halosilane, may result from the preparation of the above described acryl-functional halosilane, wherein at least a trace of each component mentioned can be found at the end of the reaction. This stabilization method comprises simply contacting the mixture with the above described gas composition. Again, it is preferred that the gas composition comprise about 2 to 4 percent by volume of oxygen, most preferably 2%, the remainder being selected from the inert gases discussed supra. As before, contact between the gas composition and the crude acryl-functional halosilane may be accomplished by purging, blanketing or sparging, preferably the latter.

This aspect of the present invention finds utility in the further processing of the crude acryl-functional halosilane wherein it is exposed to temperatures capable of inducing thermal polymerization. For example, the method may be advantageously utilized to provide storage-stable crude acryl-functional halosilane compositions while these compositions await further processing. A preferred utility is the removal of low boiling components (e.g., trichlorosilane) from the crude acryl-functional halosilane and the distillation of the crude acryl-functional halosilane to produce purified acryl-functional halosilane, wherein both of these processes are generally carried out under a reduced pressure. In these applications it is imperative to saturate the crude acryl-functional halosilane with the oxygen-containing gas composition before heating it. Furthermore, since the presence of oxygen without benefit of phenothiazine induces gelation of the acryl-functional halosilane, it is critical that phenothiazine be present in the vapor spaces of the equipment employed in carrying out these processes. As in the case of the method for preparing the acryl-functional halosilane, those skilled in the art will recognize that such processes may be carried out in either a batch or continuous fashion.

In the above methods for preparing and stabilizing the acryl-functional halosilanes of the present invention, the stabilizing amounts of phenothiazine and oxygen which are to be used will greatly depend upon the desired degree of stability, the particular acryl-functional halosilane and the amount of excess halosilane (or excess unsaturated organic compound) present. Those skilled in the art will readily determine the appropriate amounts of phenothiazine and oxygen to be added in a given set of circumstances by routine experimentation based on the instant disclosure.

By way of illustration, it has been found that when gamma-methacryloxypropyltrichlorosilane is prepared from trichlorosilane and allylmethacrylate, from about 100 to 2,000 parts per million (ppm) of phenothiazine, based on the weight of the allylmethacrylate, is preferably employed while sparging the reaction mixture with a gas composition consisting of 2% by volume of oxygen and 98% by volume of nitrogen. This set of parameters also provides sufficient protection from thermal polymerization to allow storage of the above mixture under a blanket of 2% (volume) oxygen in nitrogen. Devolatilization of the above mixture, whereby residual trichlorosilane, allylmethacrylate and low boiling by-products are removed at about 20-25 mm Hg, and batch distillation of the product gamma-methacryloxypropyltrichlorosilane at about 1-10 mm Hg are also advantageously carried out by sparging the above gas composition into the pot. In the case of continuous distillation, the mixture is well stabilized when the gas composition is sparged into the feed line. As noted above, however, the devolatilization and distillation procedures must provide for the presence of phenothiazine in the respective vapor spaces of the equipment utilized therefor.

EXAMPLES

The following examples are presented to further illustrate the methods of this invention, but are not to be construed as limiting the invention, which is delineated in the appended claims. All parts and percentages in the examples are on a weight basis unless indicated to the contrary. All viscosities are reported at 25° C. unless indicated to the contrary.

EXAMPLES 1-5

A liquid mixture was prepared by adding 150 ppm (parts per million) of phenothiazine to 300 grams of distilled gamma-methacryloxypropyltrichlorosilane. To this mixture, there was added 0.11 ml of a chloroplatinic acid complex of divinyltetramethyldisiloxane which contained 4.26% platinum and was prepared according to the methods of U.S. Pat. No. 3,419,593 to Willing, cited supra. It was thus calculated that the platinum concentration in the resulting composition was $2 \times 10^{-5}$ mole platinum per mole of silicon atoms.

A 25×200 mm PYREX test tube was fitted with a rubber stopper through which a gas inlet tube extended to the bottom of the test tube. A second tube penetrated the stopper to provide a gas outlet which was connected to a gas bubbler. A 40 ml portion of the above liquid mixture was introduced to the test tube and a dried gas composition of either pure nitrogen or oxygen-containing nitrogen, as indicated in Table 1, was supplied to the inlet tube. The gas composition was sparged through the above described mixture and exited through the outlet tube, the gas bubbler provided a back-pressure of about 100 mm Hg which prevented ingress of ambient air. The liquid mixture was thusly sparged for several minutes, whereupon there was added to the test tube 5 ml of a 1:2 molar blend of allylmethacrylate: trichlorosilane which contained 159 ppm of phenothiazine. The total mixture thus contained an excess of the trichlorosilane and simulated an intermediate composition during the preparation of gamma-methacryloxypropyltrichlorosilane. After several minutes, the test tube was partially submerged in an oil bath while the gas composition continued to be sparged through the liquid mixture. This procedure was repeated using different sparge gas compositions and bath temperatures, as indicated in Table 1. Viscosities after 22 and 43 hours, as well as gel times, of the total mixtures are presented in Table 1.

TABLE 1

Stability of gamma-Methacryloxypropyltrichlorosilane Containing an Excess of Trichlorosilane and 150 ppm Phenothiazine

| Example | Bath Temperature (°C.) | Sparge Gas Composition (Volume %) | Viscosity After 22 hr (cS) | Viscosity After 43 hr (cS) | Gel Time (hr) (Comparative) |
|---|---|---|---|---|---|
| Example 1 | 120 | Nitrogen | — | — | 3 |
| Example 2 | 120 | 4% O$_2$ | 4.05 | — | no gel @ 22 |
| Example 3 | 120 | 2% O$_2$ | 3.68 | 4.07 | no gel @ 43 |
| Example 4 | 100 | 4% O$_2$ | 3.80 | 4.05 | no gel @ 43 |
| Example 5 | 100 | 2% O$_2$ | 3.76 | 4.02 | no gel @ 43 |

It can be seen from Table 1 that the method of the present invention provides significant improvement in stability of the gamma-methacryloxypropyltrichlorosilane in the presence of phenothiazine, platinum catalyst, allylmethacrylate and an excess of trichlorosilane.

EXAMPLES 6-10

The procedures of Examples 1-5 were followed with the exception that, after the gamma-methacryloxypropyltrichlorosilane, phenothiazine and platinum catalyst were sparged with the gas composition, 5 ml of a of 2:1 molar blend of allylmethacrylate: trichlorosilane which contained 210 ppm of phenothiazine was added to the test tube. The total mixture thus contained an excess of the allylmethacrylate. Sparging with nitrogen or oxygen-containing nitrogen was again carried out at the temperatures indicated in Table 2, wherein the viscosities and gel times of such total mixtures is presented.

TABLE 2

Stability of gamma-Methacryloxypropyltrichlorosilane Containing an Excess of Allylmethacrylate and 150 ppm Phenothiazine

| Example | Bath Temperature (°C.) | Sparge Gas Composition (Volume %) | Viscosity After 22 hr (cS) | Viscosity After 43 hr (cS) | Gel Time (hr) (Comparative) |
|---|---|---|---|---|---|
| Example 6 | 120 | Nitrogen | — | — | about 22 |
| Example 7 | 120 | 4% O$_2$ | 3.97 | — | no gel @ 22 |
| Example 8 | 120 | 2% O$_2$ | 3.56 | 4.23 | no gel @ 43 |
| Example 9 | 100 | 4% O$_2$ | 3.46 | 3.91 | no gel @ 43 |
| Example 10 | 100 | 2% O$_2$ | 3.47 | 3.79 | no gel @ 43 |

It can again be seen from Table 2 that, even though the stability in nitrogen alone is somewhat better when an excess of allylmethacrylate is present, the method of the present invention still provides significant improvement in stability of the gamma-methacryloxypropyltrichlorosilane in the presence of phenothiazine, platinum catalyst, allylmethacrylate and trichlorosilane.

EXAMPLES 11-13

The procedures of Examples 1-5 were followed wherein the amount of phenothiazine was increased to 1075 ppm. Again, 5 ml of a 1:2 molar blend of allylmethacrylate:trichlorosilane which contained 1190 ppm of phenothiazine was added to 40 ml of the liquid mixture to provide a total mixture having an excess of the trichlorosilane. Results of stability testing, wherein either nitrogen or 2% (volume) oxygen in nitrogen sparge gases were employed, are shown in Table 3.

TABLE 3

Stability of gamma-Methacryloxypropyltrichlorosilane Containing an Excess of Trichlorosilane and 1075 ppm Phenothiazine

| Example | Bath Temperature (°C.) | Sparge Gas Composition (Volume %) | Viscosity 23 hr (cS) | After 72 hr (cs) (Comparative) |
|---|---|---|---|---|
| Example 11 | 120 | Nitrogen | 8.22 | 9.32 |
| Example 12 | 120 | 2% O₂ | 3.84 | 4.45 |
| Example 13 | 100 | 2% O₂ | 3.62 | 4.24 |

From Table 3 it can be seen that increasing the phenothiazine content in the total mixtures did result in improved stability when only nitrogen was used as the sparge gas since the mixtures did not gel. However, sparging with the gas containing 2% (volume) oxygen resulted in much lower viscosities. Thus, lower levels of phenothiazine may be used to stabilize such mixtures when the sparge gas contains oxygen, according to the method of the present invention.

EXAMPLES 14

A one liter three-neck flask, equipped with a thermometer, stirrer, sparge tube, addition funnel and a condenser, was well purged with nitrogen. The condenser was vented to a trap which provided 1 inch Hg back pressure to the system to prevent the ingress of air. There was then added to the flask 378.6 grams (3.0 moles) of allylmethacrylate which contained 0.113 grams of phenothiazine (298 ppm) and 0.288 grams of the catalyst containing 4.26% platinum which was employed in the above examples. The addition funnel was then charged with 426.9 grams (3.15 moles) of trichlorosilane and the sparge gas was changed to a composition of 2% by volume of oxygen and 98% by volume of nitrogen. This sparge was continued for one hour at a rate of 420 cc/min. The sparge rate was then reduced to 85 cc/min. and the contents of the flask were heated to 112° C. The trichlorosilane was added over a period of one hour while the temperature of the reaction mixture was maintained between 112° and 122° C. As in the previous examples, it was calculated that the platinum concentration was $2 \times 10^{-5}$ mole platinum per mole of silicon atoms.

When the addition was completed, the reaction mixture was observed to have a viscosity of 2.58 cS. After heating the reaction mixture at 114-127° C. for two more hours using the oxygen-containing sparge, the viscosity increased to only 2.94 cS. At this point, a portion of the reaction mixture was further evaluated with respect to gel formation. This test consisted of placing 6 drops of the reaction mixture in 2 grams of heptane. Since acrylate polymers are quite insoluble in heptane, the absence of a precipitate indicated that little or no polymer had formed during the reaction and subsequent heating.

The addition funnel and condenser were replaced with an eight inch Vigreux column and the reaction mixture was distilled at a pressure of 4-5 mm Hg in the absence of a purge gas. This distillation yielded 680.5 grams of gamma-methacryloxypropyltrichlorosilane having a purity of 98%, while leaving only 19.16 grams of a viscous residue in the flask. This represented a recovery of 86.7%.

(COMPARATIVE) EXAMPLE 15

The procedures of Example 14 were repeated with the exception that nitrogen alone was used to purge the flask and sparge the reaction mixture. The addition of the trichlorosilane took about one hour, after which the viscosity of the reaction mixture was observed to be 15.19 cS and the heptane compatability test (see Example 14) indicated that polymer had formed. Additional heating at 120° C. for one hour resulted in a reaction mixture having a viscosity of 83.5 cS. At this point, solid particles of polymer were visible in the reaction mixture, which particles appeared to increase in size with additional heating.

I claim:

1. A method for making an acryl-functional halosilane having the general formula

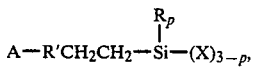

comprising reacting an unsaturated organic compound having the formula A—R'CH=CH₂ with a halosilane having the formula

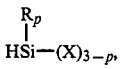

in which A is a group selected rom acryloxy or methacryloxy radicals, R' is selected from a divalent hydrocarbon radical having 1 to 11 carbon atoms, an aryl group or an aryl-containing alkylene group, R is selected from alkyl radicals having 1-6 carbon atoms or the phenyl radical, X is selected from chlorine or bromine radicals and p is 0, 1 or 2, in the presence of a platinum hydrosilation catalyst and a stabilizing amount of phenothiazine, wherein the reaction mixture is contacted with a gas composition comprising at least 0.1 percent by volume of oxygen.

2. The method of claim 1, wherein A is the methacryloxy radical.

3. The method of claim 2, wherein X is chlorine.

4. The method of claim 3, wherein R' is methylene group.

5. The method of claim 4, wherein R is the methyl radical.

6. The method of claim 5, wherein said acryl-functional halosilane is gamma-methacryloxypropyltrichlorosilane.

7. The method of claim 6, wherein said gas composition comprises from about 2 to 4 percent by volume oxygen.

8. A method for stabilizing a mixture of an acryl-functional halosilane, an unsaturated organic compound, a halosilane and a platinum hydrosilation catalyst and a stabilizing amount of phenothiazine, comprising contacting said mixture with a gas composition comprising at least 0.1 percent by volume of oxygen, wherein said acryl-functional halosilane has the general formula

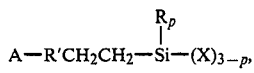

said unsaturated organic compound has the formula A—R'CH=CH$_2$ and said halosilane has the formula

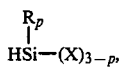

in which A is a group selected from acryloxy or methacryloxy radicals, R' is selected from a divalent hydrocarbon radical having 1 to 11 carbon atoms, an aryl group or an aryl-containing alkylene group, 11 carbon atoms, R is selected from the group consisting of alkyl radicals having 1-6 carbon atoms and the phenyl radical, X is selected from chlorine or bromine radicals and p is 0, 1 or 2.

9. The method of claim 8, wherein A is the methacryloxy radical.

10. The method of claim 9, wherein X is chlorine.

11. The method of claim 10, wherein R' is methylene group.

12. The method of claim 11, wherein R is the methyl radical.

13. The method of claim 12, wherein said acryl-functional halosilane is gamma-methacryloxypropyltrichlorosilane.

14. The method of claim 13, wherein said gas composition comprises from about 2 to 4 percent by volume oxygen.

15. The method of claim 8, wherein said mixture is distilled at reduced pressure.

16. The method of claim 9, wherein said mixture is distilled at reduced pressure.

17. The method of claim 10, wherein said mixture is distilled at reduced pressure.

18. The method of claim 11, wherein said mixture is distilled at reduced pressure.

19. The method of claim 12, wherein said mixture is distilled at reduced pressure.

20. The method of claim 13, wherein said mixture is distilled at reduced pressure.

* * * * *